United States Patent [19]
Giele et al.

[11] Patent Number: 5,238,007
[45] Date of Patent: Aug. 24, 1993

[54] PACING LEAD WITH IMPROVED ANCHOR MECHANISM

[75] Inventors: Vincent Giele; Frits M. van Krieken, both of Dieren; Frederik H. M. Wittkampf, Brummen, all of Netherlands

[73] Assignee: Vitatron Medical B.V., Dieren, Netherlands

[21] Appl. No.: 806,689

[22] Filed: Dec. 12, 1991

[51] Int. Cl.$^5$ ............................................. A61N 1/05
[52] U.S. Cl. .................................... 607/126; 128/642
[58] Field of Search ................. 128/642, 784, 785, 786

[56] References Cited

U.S. PATENT DOCUMENTS

| | | | |
|---|---|---|---|
| 3,902,501 | 9/1975 | Citron et al. | 128/418 |
| 4,419,819 | 12/1983 | Dickhudt et al. | 29/857 |
| 4,597,118 | 9/1990 | Erlebacher | 128/785 |
| 4,721,118 | 1/1988 | Harris | 128/785 |
| 4,913,164 | 4/1990 | Greene et al. | 128/785 |

FOREIGN PATENT DOCUMENTS 3300050  7/1984  Fed. Rep. of Germany .

Primary Examiner—Kyle L. Howell
Assistant Examiner—Scott M. Getzow
Attorney, Agent, or Firm—Woodcock Washburn Kurtz Mackiewicz & Norris

[57] ABSTRACT

A pacing lead is disclosed having folded tine elements in a first normal state, the tine elements being adapted to be unfolded by insertion of a stylet. In the second unfolded state, the tine elements are stretched to conform closely to the outer diameter of the lead casing, providing a reduced cross-section that facilitates introduction of the lead, and repositioning of the lead tip. A telescoping arrangement of inner and outer tubing elements is used to enable the stretching of the tine elements.

22 Claims, 3 Drawing Sheets

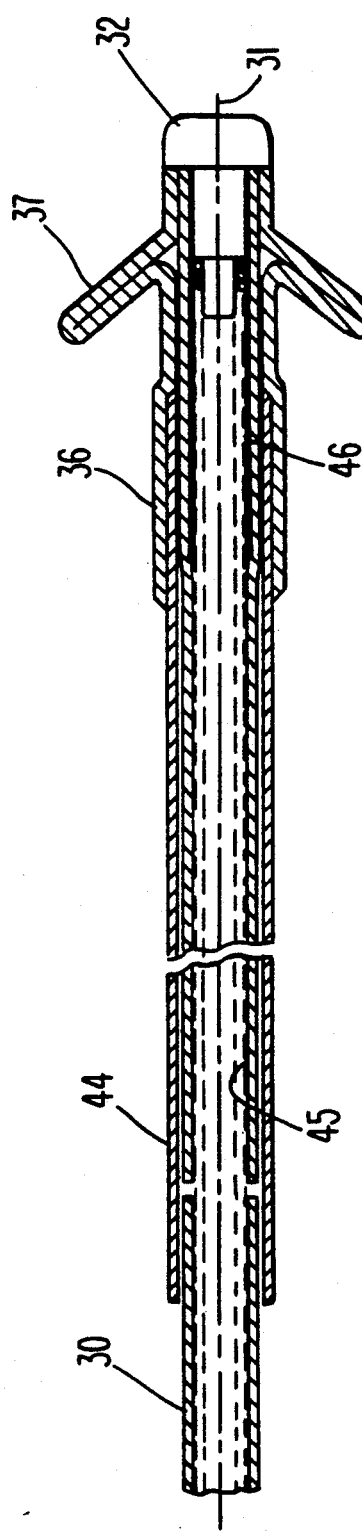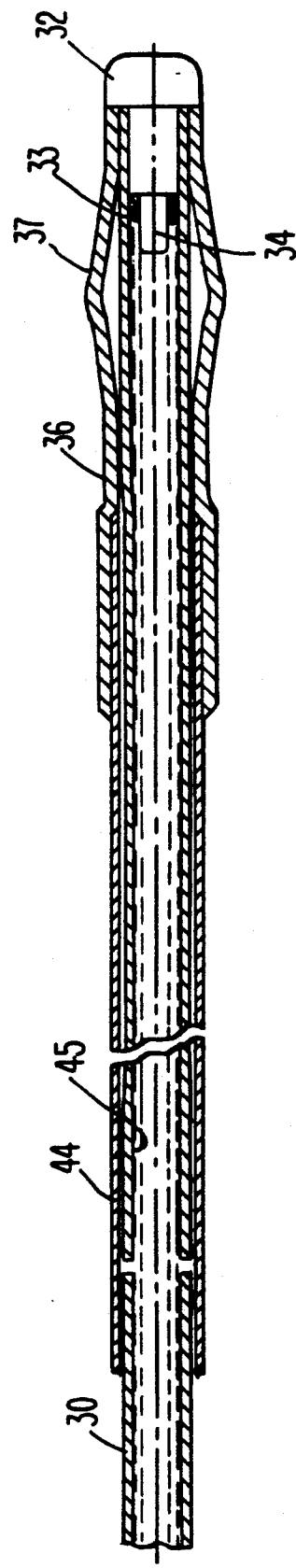

PACING LEAD WITH IMPROVED ANCHOR MECHANISM

BACKGROUND OF THE INVENTION

1. Field of the Invention

This invention relates to pacing leads having an anchoring mechanism such as tines and, more particularly, a lead having means for changing the peripheral geometry of the anchor mechanism to provide a reduced cross-section at times of introduction of the lead and/or repositioning of the lead.

2. Background of the Prior Art

Pacing leads using an anchoring mechanism for anchoring the distal tip with respect to the inside of the heart are well known and very important to a successful pacing system. The most successful and widely used anchoring mechanism is that of tines, as disclosed in U.S. Pat. No. 3,902,501, assigned to Medtronic, Inc. The tined lead provides a plurality of pliant tines that extend from an area adjacent the distal tip and electrode of the lead, the tines forming an acute angle with the lead body. The tines are effective in engaging the trabeculae found in the ventricle as well as the atrium, to maintain the electrode tip in a secure position after the physician has positioned it for good pacing threshold.

While the tined lead has been highly successful, it has carried one longstanding drawback, namely the problems associated with the lateral projections of the tines at the time of introduction of the lead and/or in attempting to reposition the lead. Basically, the lateral extension of the tines causes an effective increased diameter of the lead at about the distal tip, i.e., the effective diameter is much greater at the distal tip than it is along the length of the lead, which length has a suitable uniform small outer diameter. The tines can get stuck at the time of introduction, particularly in passing through the valve between the atrium and the ventricle for positioning against the inner wall of the right ventricle. Further, once the physician has positioned the distal tip against the heart wall, it may be desirable to change that position, in either acute or chronic situations, to obtain a position which offers improved pacing threshold; or to withdraw the lead entirely. In such a situation, withdrawal of the tined anchor mechanism may be difficult, or even impossible, to do without damage to the trabeculae or to a valve.

The difficulty of introducing a pacing lead with a tined anchoring element was recognized in the first patent on the tined lead, the above-noted Citron et al. U.S. Pat. No. 3,902,501. That patent showed an embodiment which included a mechanism for holding the tines against the electrode body during insertion, while allowing their release once the tip was positioned in proximity to the heart wall. However, the mechanism disclosed has not been effective in achieving the aim of reducing the tip cross-section while reliably providing for release of the tines after insertion of the lead. Further, this mechanism did not have any capability of transforming the tines into a reduced cross-sectional geometry which would permit easier withdrawal of the anchor when and as desired. What remained necessary at that time, and still remains a need in the art, is a design which provides both for avoiding the lateral extension of the tines or other anchor mechanism during introduction, and also one which can withdraw the tines in such a manner as to provide improved characteristics for withdrawing the lead after it has already been positioned against the heart wall.

Since the introduction and commercial success of the tined lead, there have been a number of efforts in the pacing industry, and disclosed in the patent literature, to provide an anchoring mechanism which would provide improved characteristics for minimizing the above-noted problems at introduction and/or repositioning. German Application 33 00 050 discloses an intravenous heart pacemaker electrode having a fixation or anchor means that can be shifted along the longitudinal axis of the lead in a manner so as to reduce the effective diameter of the anchor mechanism. However, this design is applicable only for a lobe-type anchor element, and it does not suggest a solution to the problem with respect to tines which extend laterally to a free end. Another patent disclosing an extensible passive fixation mechanism for a pacing lead is U.S. Pat. No. 4,913,164. This patent shows a mechanism for moving tine-type elements from a first unextended position to a second extended position, or vice versa. However, the mechanism is complex, and the technique of closing the tine-type elements would tend to ensnare the lead tip in prior-engaged trabeculae, rather than provide easy withdrawal. The Earlebacher U.S. Pat. No. 4,957,118 shows another form of electrode lead having a tine assembly, wherein the tines can be actively moved back and forth between a retracted position and an extended position. However, the mechanism of this disclosure likewise results in a similar problem for extraction, namely the tine element is brought down over or on top of the engaging trabeculae. Further, when in the closed position, the tine end is free and provides a space between the tube casing and the tine which would snag trabeculae when the physician attempts to withdraw the lead.

There remains a need in the art for a pacing lead which provides an effective anchoring mechanism when the lead is in position, but having means to reduce the effect of such anchoring mechanism when desired, such as during introduction or repositioning of the lead. Stated differently, there is a need for reducing the effective cross-section of an anchor mechanism such as found in a tined pacing lead, whereby the anchor mechanism is transformed to a geometry which as closely as possible merges with the cylindrical lead casing, and which does not obstruct withdrawal of the lead when in the transformed state.

SUMMARY OF THE INVENTION

In view of the above-noted unresolved needs of the prior art, it is an object of this invention to provide an improved implantable lead for pacing and/or other applications, the lead having an anchoring mechanism at its tip end which in its normal state provides for fixation of the tip end to the inner heart wall, and which is transformable into a second state wherein the fixation mechanism is transformed to lie substantially parallel to the lead axis. In the second state, the fixation mechanism presents a reduced effective outer diameter and a substantially continuous smooth outer surface extending proximally back from the lead tip. The lead comprises a telescoping mechanism which is provided at its distal end for axial movement of a portion of the anchoring mechanism, for changing it from a normal state to a temporarily transformed state. In another embodiment, a lead or catheter has an axially movable element at its distal end, which may be an anchoring element, which is movable from one position to another by the telescoping arrangement.

The preferred embodiment of the lead of this invention is a pacing lead which has a casing running the length thereof to about the distal tip end, the casing being substantially concentric to a longitudinal axis of the flexible lead. A 2-state flexible anchor member is positioned near the distal tip, having a first normal rest state which provides fixation to the heart wall in the form of tines, and a second state wherein the anchor member is extended longitudinally to approximate the smooth uniform outer casing of the lead, thereby minimizing the impact of the anchor member during positioning or repositioning of the lead. The lead preferably has a telescoping arrangement comprising a first outer tubing element which is connected to the lead casing and the anchor member, and a second inner tubing element which is movable within the first tubing element to move the lead tip between a normal and extended position, which movement in turn causes transformation of the flexible anchor member (tines) from one state to another. The movement is provided by a stylet which is inserted through the lead lumen to provide a force against the tip end; a clamping mechanism is provided to hold the tines in a stretched position. The lead design also provides effective sealing at the distal end to prevent leakage of body fluid through the anchor mechanism into the interior length of the lead.

BRIEF DESCRIPTION OF THE DRAWINGS

FIGS. 2A and 2B illustrate a second embodiment of the lead of this invention, again illustrating the difference between the normal and extended positions.

DESCRIPTION OF THE PREFERRED EMBODIMENT

Figure 1A:
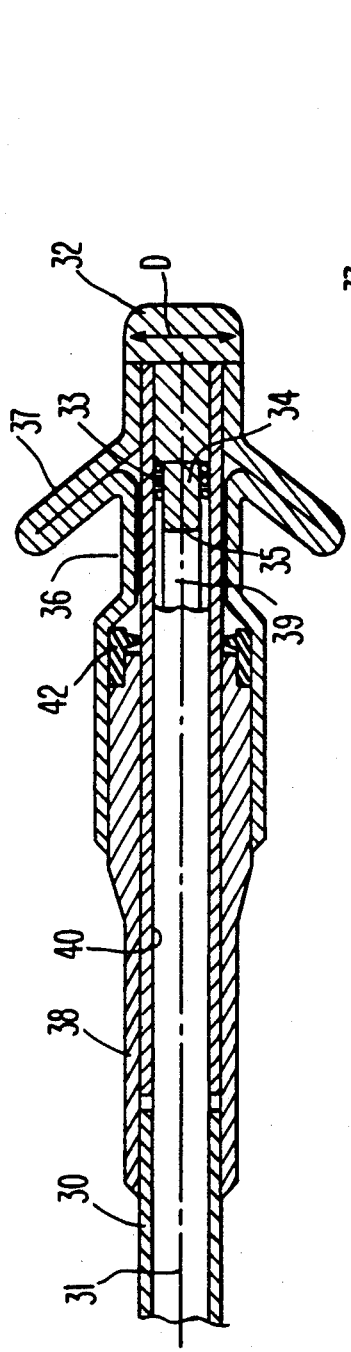
FIGS. 1A, 1B and 1C illustrate the distal end of a preferred embodiment of the lead of this invention, and in particular illustrate the nature of the anchor mechanism and the difference between the normal and the extended positions.
Figure 1B:
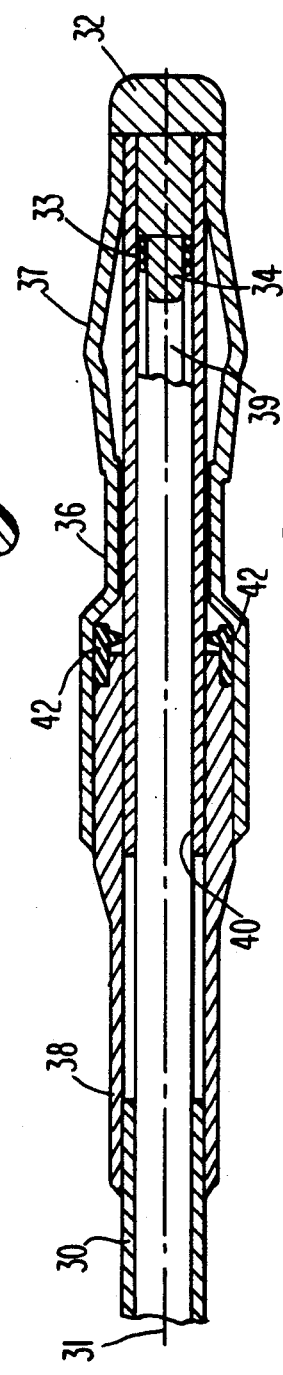
Figure 1C:
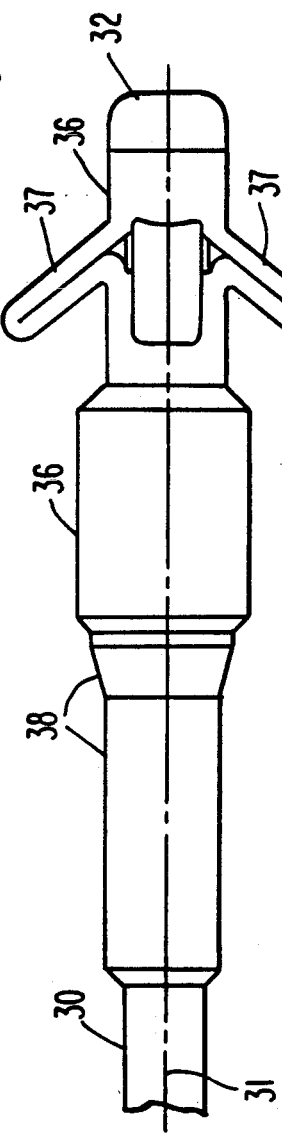
Figure 1D:
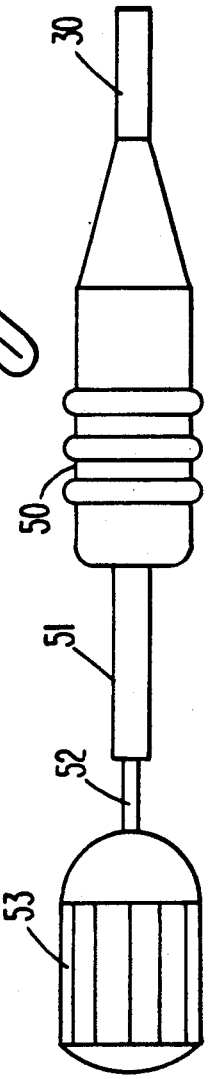
FIG. 1D illustrates the proximal end of the lead and insertion of a stylet.

Referring now to FIGS. 1A through 1D, there are shown representations of the preferred embodiment of this invention. The lead of this embodiment has a casing 30 which runs substantially the length of the lead from the proximal end, to a point approaching the distal end, as seen in FIGS. 1A and 1D. For a unipolar lead, a suitable casing material is PUR55D; for a bipolar lead, a less rigid material such as silicone rubber 80 SHORE A may be used. The tubing 30 is substantially cylindrical about a longitudinal axis 31, and provides a flexible lead as is well known in the art. An electrode 32 is illustrated as positioned at the extreme distal tip, for delivering pacing pulses to a patient's heart and for sensing natural heart signals. The electrode has an outer surface portion, for interfacing with the heart, and an inner proximally extending portion which has mechanical and electrical functions, as discussed below. Although not shown, another electrode, suitably in the form of a ring, may be positioned proximally from the distal tip to provide a bipolar lead. A coil 33, suitably made of MP 35N nickle cobalt alloy, with an outer diameter of about 0.8 mm, is illustrated for transmitting electrical signals between the proximal and distal ends of the lead. The coil 33 surrounds and is welded to a proximal extension, or pin 34, of electrode element 32. Coil 33 is stretchable, particularly at the distal end; the coil is pre-stressed and of a length such that it is slightly stretched when attached to the tip, so that it is normally exerting a small background force on the tip.

An anchor member 36, suitably composed of PUR 80 A, and having a wall thickness of about 0.225 mm, is connected to the lead so as to be positioned flush with electrode 32 to provide a continuous uniform outer diameter at the point where anchor member 36 is attached to tip electrode 32. In the preferred embodiment, this outer diameter may be, for example, 1.7 mm. An outer tubing 38, suitably made of PUR 75 D, is adhered to the distal end of the casing 30, by a suitable adhesive and/or mechanical locking. Outer tubing 38 extends distally toward the tip end, and a proximal portion of anchor member 36 is affixed by a suitable adhesive and/or mechanical locking to the outside of the distal end of tubing 38. Inner tubing 40, suitably made of PUR 75 D, is positioned inside of outer tubing 38 in a telescopic relation, such that it can move longitudinally relative to tubing 38, and just inside of tubing 38. Inner tubing 40 is adhered to electrode element 32 and/or to the distal portion of anchor 36 by a suitable adhesive and/or mechanical locking. By this arrangement, when an axial force is applied to tip 32, as by a stylet, inner tubing 40 and the distal end of anchor member 36 that is attached to tubing 40, are carried forward (distally). Such a longitudinal force may be exerted by a stylet 52, as shown in FIG. 1D, which is positioned by the physician through lumen 39 so as to abut the proximal surface 35 of electrode pin 34.

Anchor member 36, as illustrated also in FIG. 1C, is configured so that in its normal state, herein referred to as its first state, presents a plurality of extensions which extend laterally from the longitudinal axis at an acute angle. As illustrated, there are four extensions 37, constituting four tine members of recognizable form, which provide an anchoring or fixation mechanism in a known manner. The tine portions 37 comprise a folding over of each respective longitudinal tine portion 37, which fold is normally maintained in a steady state by the cut and pre-formed shape of the tine portions, and also by the resilience of coil 33. These design features normally keep electrode 32 in the position as shown in FIG. 1A, forcing the tine portions 37 into the illustrated folded position. However, as seen in FIG. 1B, when the tip 32 is extended proximally, as by a stylet, the tine portions 37 are unfolded so that they lie substantially parallel to the longitudinal axis 31. In this second state, the lateral extension of the tines is substantially eliminated, and there is no laterally extending portion of the anchor 36 that would obstruct the physician from pulling the entire lead backward (proximally) so as to remove it from the position in which it had been. Note that in FIG. 1B, inner tubing 40 is advanced proximally within outer tubing 38 and away from the end of casing 30, in a telescoping fashion. When the lead has been moved as desired, and the physician wants to return to the first tined state, the stylet is withdrawn, whereby the resilience of the stretched coil 33 together with the preformed shape of the anchor member, pulls the distal tip backward. The backward movement is limited by the formation of the folded tined portions, and by the casing 30 which would stop any further proximal movement of inner tubing 40.

Referring to FIGS. 1A and 1C, it is seen that the construction of the anchor member 36 so as to have tine portions 37 results in openings in the overall outer surface of anchor member 36. Body fluid can enter through these openings to surround the outside of casing 40. To prevent penetration of such fluid between the common surface of tubings 38 and 40, and from there into the interior coil and lumen area, a sealing member 42 is provided which is fixed at the distal end of tubing 38 and also to the inside surface of anchor member 36. This sealing ring is suitably made of silicone rubber, and provides a sliding seal on the outer surface of tubing 40. The seal is annular, so as to prevent any liquid fluid any point around the tubing. This seal enables the employment of the telescoping arrangement of tubing elements 38 and 40, while maintaining integrity of the overall distal end of the lead with respect to leakage of body fluids into the interior. In order to carry the sealing ring, the distal end of tubing 38 may be made thicker, as illustrated. The design of this lead enables use of an introducer size of 8 Fr.

Referring briefly to FIG. 1D, there is shown a representation of the proximal end of the lead. Casing 30 leads into a plug 50 of conventional design, which terminates proximally with a plug pin 51. The lumen 39, not shown in FIG. 1D, extends through the length of the casing, plug and plug tip. A stylet 52 is inserted by the physician into the plug tip and through the entire lead, for positioning as discussed above. The stylet can be manipulated, including rotated, by knob 53. Note that the outer periphery of inner tubing 40 and the inner periphery of outer tubing 38 can be formed with matching threads, such that longitudinal insertion of the stylet and extension of electrode 32 can also cause rotation of the anchor means, which may be useful in securing the best position.

Referring now to FIGS. 2A and 2B, there is shown an alternate embodiment of this invention. Rather, in this arrangement, there is a relatively rigid outer tubing 44, and an inner tubing 45 which is made of a more flexible material, i.e., a silicone tube, 50 SHORE A. Tube 45 is attached by a suitable adhesive at its proximal end to tube 45, sealing off any path for moisture to pass to the interior of the lead. The silicone tubing 45 not only performs the sealing action, but acts as a spring to assist the anchor element in returning to the rest position when the stylet is withdrawn. In this embodiment as well, the coil also assists in returning the tines to the first state, or rest position. In addition, shrink tubing 46, suitably made of PTFE or TEFZEL, is also affixed by adhesive to the inside wall of tubing 45, to prevent the tip of the stylet from puncturing the tubing in the event that the stylet is curved or bent relative to the longitudinal axis 31 of the tube. This embodiment enables use of an introducer size of 6 Fr.

Figure 3:
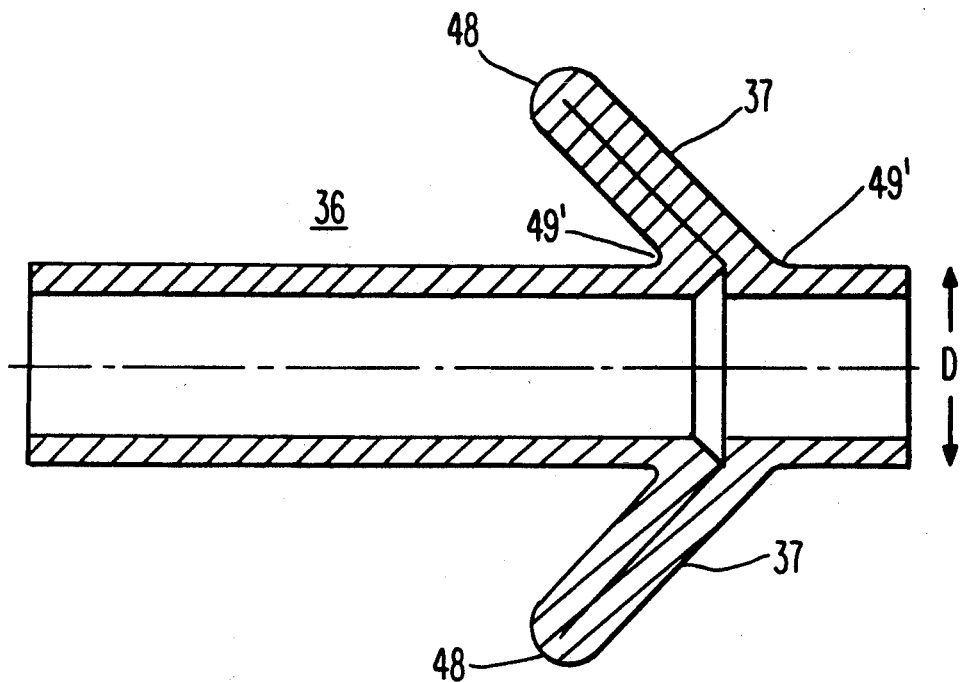
FIG. 3 is a detailed drawing of the foldable tine anchor mechanism for this invention, in the preformed folded state.

FIG. 3 is a cross-section of an anchor element 36 illustrating the tine portions 37 in their pre-formed state 1. The thermoplastic elastomer element 36 is first molded, and then heat deformed into the state illustrated in FIG. 3. The outer diameter D of the far distal end, which abuts a back annular wall of the front portion of electrode element 32, is nominally 1.7 mm. The area of each portion 37 where the bend occurs, designated 48, is curvilinear on both the outside surface and the inner surface, as seen in FIG. 1B, to induce the folding of the tine so as to facilitate the normal folded tine position seen in FIG. 1A. Also, the outer surface at points 49', which define the two ends of the folded region, or either one of them, may be notched so as to facilitate folding of portion 37 into the tine configuration. The respective inner and outer diameters of the different portions are conformed to fit over the inner and outer tubing respectively, as shown in FIGS. 1A, 1B, 2A and 2B.

Figure 4:
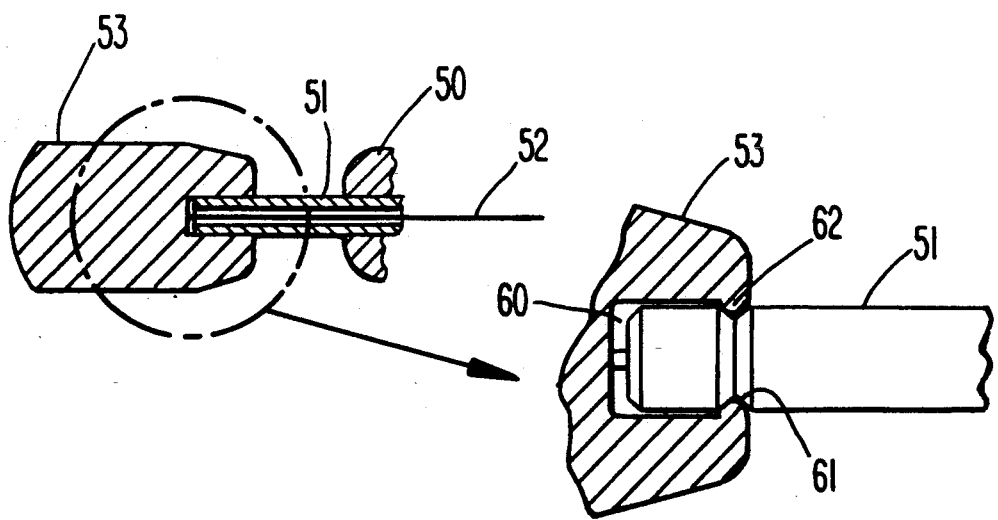
FIG. 4 is an illustration of a clamping mechanism for holding the stylet so that the tines are in the stretched state.

Referring now to FIG. 4, there is illustrated a mechanism for locking the stylet to the lead, so that the tines or other tip element are maintained in an extended position while the lead is positioned. The stylet 52 is carried by and movable within knob 53. The knob has a receiving cavity 60 for receiving the proximal end of plug pin 51. Pin 51 has an annular notch 61, and knob 53 has a flexible annular collar 62 which can be snapped into notch 61, to hold the knob in place relative to the lead. Knob 53 also can be rotated so as to grip the stylet, whereby the stylet becomes fixed in position relative to the lead. Other equivalent clamping means may be employed for the purpose of clamping the stylet to hold the lead distal tip in the extended state.

The telescoping arrangement illustrated in the preferred embodiments may be utilized in other types of leads, or catheters. For example, it may be utilized with a screw-in-type pacing lead, to advance or retract the screw tip at the distal end of the lead, or to advance or retract other types of fixation mechanisms. Likewise, it can be used with catheters to change the position or transform an element positioned at or near the distal end. For example, and referring to FIG. 2B, element 32 may comprise a fixation member, such as a screw tip; and element 36 can be a simple stretchable cylindrical tubing, whereby the stylet is used to urge it forward and to twist it, for penetration into the heart wall.

What is claimed is:

1. A lead for transmitting electrical signals between a first proximal end and a second distal end adapted to be positioned within a patient's body, said lead having at least one electrode positioned at about a distal tip thereof and having at least one conductor for transmitting electrical signals between said proximal and distal ends, said at least one conductor being connected to said electrode, said lead having at least a section at its distal end which is stretchable, said lead having a flexible casing running most of the length thereof substantially concentric to the longitudinal axis of said lead, a 2-state flexible anchor member positioned near said distal end, having at least one tine portion characterized by a first normal state wherein it comprises a tine, said tine portion being transformable to a second state wherein it is extended longitudinally so as to be close to said longitudinal axis, a first outer tubing element having proximal and distal ends, the first tubing element proximal end being connected to said casing and said first tubing element distal end being connected to said anchor member, a second inner tubing element having proximal and distal ends, said second tubing element distal end being connected to said tip or said anchor member at about the distal end of said lead and being slidable relative to said first tubing element, and sealing means positioned between said first and second tubing elements for preventing the passage of fluid between said two elements.

2. The lead as described in claim 1, wherein said flexible anchor member comprises a wall having a radial thickness limited to about 1.7 mm.

3. The lead as described in claim 1, wherein said electrode has a diameter transverse to said longitudinal axis limited to about 1.7 mm.

4. The lead as described in claim 3, wherein said anchor member has a cylindrical portion which is attached to abut said tip, the outer dimension of said cylindrical portion being substantially the same as said electrode transverse diameter.

5. The lead as described in claim 1, wherein said anchor member (36) comprises a plurality of tine portions, each of said portions being flexible to form either of said first and second states.

6. The lead as described in claim 5, wherein said lead comprises a substantially central lumen extending along said longitudinal axis, whereby a stylet can be inserted through said lumen against said tip electrode to stretch said anchor member tine portions into said second state.

7. The lead as described in claim 6, in combination with a stylet inserted through said lumen and engaging said tip electrode so as to push it in a distal direction, whereby said flexible tine portions are transformed into said second state.

8. The lead as described in claim 1, wherein said anchor member has four tine portions spaced circumferentially from each other, each of said tine portions being characterized by having a said first state and being transformable into a said second state.

9. The lead as described in claim 1, wherein said tine portion is shaped with a curve for facilitating said portion to be folded into said first state.

10. The lead as described in claim 1, wherein said tine portion is pre-formed to normally be in a folded tine state.

11. The lead as described in claim 1, wherein said wire is a coil which is pre-stressed to normally apply a force to maintain said tine portion in said first tine state.

12. The lead as described in claim 1, wherein said tine portion has a notch on an end thereof, said notch facilitating said portion to normally be in said first state.

13. A pacing lead having a distal tip, an annular fixation member at about said distal tip, said fixation member being made of a flexible material, said fixation member having a plurality of normally folded tine portions which present laterally extending tines when in a first normal state, and extending means for permitting the extension of one end of said fixation member longitudinally relative to its other end causing said tine portion to assume a second state wherein said tine portions are unfolded and lie substantially parallel to the lead longitudinal axis, and wherein said extending means comprises first and second concentric tubing members, said second tubing member being positioned within said first tubing member and being telescopically movable relative thereto.

14. The lead as described in claim 13, having a casing which extends substantially the length of said lead, wherein said fixation member has a proximal end, said fixation member being fixed at its proximal end to said lead casing, and wherein said extending means enables extension of said tine portions relative to said fixed proximal end.

15. The lead as described in claim 13, wherein when a said tine portion is in its second extended state, it is configured so that its surface presents no obstruction to proximal positioning of said lead.

16. A catheter adapted for being inserted into a patient, said catheter having a distal end, a flexible cylindrical casing running substantially the length thereof and defining a longitudinal axis, a first outer tubing element having proximal and distal ends, said first tubing element proximal end being connected to said casing, a second inner tubing element positioned within and unattached to said first element, said second inner tubing element presenting an interior wall substantially the same diameter as said tube casing and extending to about the distal end of said catheter, a stretchable element fixed to said outer tubing element and to the distal end of said inner tubing element, and a tip element positioned at said distal end of said catheter and attached to said stretchable element and said inner tubing element, whereby said tip element can be extended distally relative to said tube casing.

17. The catheter as described in claim 16, wherein said tip element is a fixation element.

18. A lead for transmitting electrical signals between a first proximal end and a second distal end of said lead and adapted to be positioned within a patient's body, said lead having at least one electrode positioned at about said distal end and having at least one conductor for transmitting electrical signals between said proximal and distal ends, said at least one conductor being connected to a tip of said distal end and having at least a section at its distal end which is stretchable, said lead having a flexible casing running most of the length thereof substantially concentric to the longitudinal axis of said lead, said casing having a distal end, a 2-state flexible anchor member positioned near said distal tip, having at least one tine portion characterized by a first normal state wherein it comprises a tine, said tine portion being transformable to a second state wherein it is extended longitudinally so as to be close to said longitudinal axis, a first outer tubing element having proximal and distal ends, the first tubing element proximal end being connected to said casing and said first tubing element distal end being connected to said anchor member, a second inner tubing element having proximal and distal ends, said second tubing element proximal end being sealingly attached to said outer tubing element near said distal end of said casing, and said second tubing element distal end being connected to said tip or said anchor member at about the distal end of said lead and being slidable relative to said first tubing element, whereby movement of said distal tip relative to said casing causes transformation of said anchor member from said first normal state to said second state.

19. The lead as described in claim 18, in combination with a stylet inserted through said lead to bear against said distal tip.

20. The lead as described in claim 19, further comprising locking means for locking said stylet in a position whereby it maintains a force on said distal tip so as to hold said anchor member in said second state.

21. The lead as described in claim 18, wherein said anchor member comprises a plurality of tine portions preformed in said first normal state.

22. The lead as described in claim 21, wherein said conductor distal section is a coil, whereby the spring action of said coil and said preformed tine portions act to normally place said tine portions in said normal state.

* * * * *